United States Patent
Guillermet-Guibert et al.

(10) Patent No.: US 11,351,156 B2
(45) Date of Patent: Jun. 7, 2022

(54) COMBINATION TREATMENT OF PANCREATIC CANCER

(71) Applicants: INSERM (Institut National de la Santé et de la Recherche Médicale), Paris (FR); Université Paul Sabatier Toulouse III, Toulouse (FR); Centre National de la Recherche Scientifique (CNRS), Paris (FR); Klinikum Rechts der Isar der Technischen Universität München, Munich (DE)

(72) Inventors: Julie Guillermet-Guibert, Toulouse (FR); Maximillian Reichert, Munich (DE); Célia Cintas, Toulouse (FR)

(73) Assignees: INSERM, Paris (FR); Université Paul Sabatier Toulouse III, Toulouse (FR); CNRS, Paris (FR); Klinikum Rechts der Isar der Technischen Universität München, Munich (DE)

( * ) Notice: Subject to any disclaimer, the term of this patent is extended or adjusted under 35 U.S.C. 154(b) by 0 days.

(21) Appl. No.: 16/755,390

(22) PCT Filed: Oct. 12, 2018

(86) PCT No.: PCT/EP2018/077868
§ 371 (c)(1),
(2) Date: Apr. 10, 2020

(87) PCT Pub. No.: WO2019/073031
PCT Pub. Date: Apr. 18, 2019

(65) Prior Publication Data
US 2021/0205276 A1    Jul. 8, 2021

(30) Foreign Application Priority Data
Oct. 13, 2017  (EP) .................................. 17306391

(51) Int. Cl.
*A61K 31/427* (2006.01)
*A61P 35/00* (2006.01)
*A61K 31/5377* (2006.01)

(52) U.S. Cl.
CPC ........ *A61K 31/427* (2013.01); *A61K 31/5377* (2013.01); *A61P 35/00* (2018.01)

(58) Field of Classification Search
CPC .................................................... A61K 31/427
USPC ....................................................... 514/233.2
See application file for complete search history.

(56) References Cited

FOREIGN PATENT DOCUMENTS

| WO | 2004/029055 A1 | 4/2004 |
|----|----------------|--------|
| WO | 2011/130628 A1 | 10/2011 |
| WO | 2012/052745 A1 | 4/2012 |
| WO | 2013/049581 A1 | 4/2013 |

OTHER PUBLICATIONS

Baer et al., Genes and Development (2014) vol. 28(23), pp. 2621-2635. (applicant's own work).*
Edling et al., Canc. Biol. & Therapy (2014), 15(5), pp. 524-532.*

* cited by examiner

*Primary Examiner* — Taofiq A Solola
(74) *Attorney, Agent, or Firm* — WC&F IP

(57) ABSTRACT

PI3K signalling is the most increased pathway in human cancers. The four isoforms of PI3K are thought to be activated by different redundant mechanisms leading to a common downstream signalling. The inventors questioned this concept, by mapping differential isoform-specific downstream signalling in response to their constant selective inhibition in pancreatic cancer, a disease currently without therapy. They identified common and specific signals activated by each PI3K isoform. These data make the rational for the development of highly selective PI3K isoform drugs used in combination, instead of compounds inhibiting all PI3Ks. In particular, the inventors showed that combined p110α and 110γ inhibition is the most efficient strategy for pancreatic cancer patients.

2 Claims, 7 Drawing Sheets

COMBINATION TREATMENT OF PANCREATIC CANCER

FIELD OF THE INVENTION

Figure 1A:
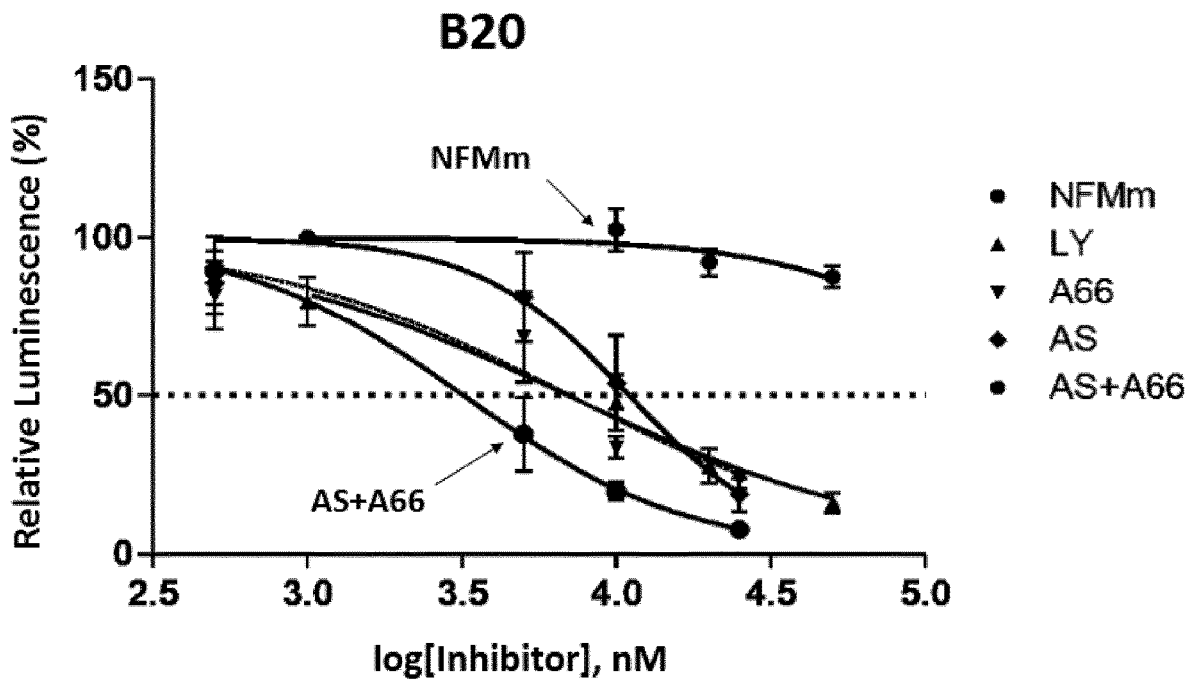

The present invention relates to combination treatment of pancreatic cancer.

BACKGROUND OF THE INVENTION

New strategies are needed for the cure of pancreatic cancer patients, due to dramatic lethality rate of this disease. PI3K signalling as assessed by Akt phosphorylation or PI3K/Akt/mTOR gene signature is increased and associated with poor prognosis in patients which underwent surgery [15, 16]. Even if well tolerated, the inhibition of mTOR with RAD001 monotherapy has only a minimal clinical action on gemcitabine-resistant metastatic pancreatic cancer patient (gemcitabine is the standard of line chemotherapy for these pathologies—it improves the well-being of the patient but increases their survival of only a few weeks) [17]. This result is to be correlated with the fact that mTOR inhibitors interfere with a negative feedback loop, which results in an unexpected increase of PI3K signalling and in an increase of the activity of other targets of PI3Ks also regulating proliferation and other protumoral properties. Targeting the upstream PI3K is thus expected to have a better clinical action in these patients. However, prior knowledge of cancer cell adaptation to the inhibition of upstream class I PI3K signalling would be necessary to develop efficient anti-PI3K therapeutic strategy in this disease, where so far all signal-targeted therapies have failed in clinical trials. This knowledge could have an impact to design combinations of treatments taking into account these compensation/resistance mechanisms and could explain the specific intrinsic resistance mechanisms of pancreatic cancer cells to signal-targeted therapies.

SUMMARY OF THE INVENTION

The present invention relates to combination treatment of pancreatic cancer. In particular, the present invention is defined by the claims.

DETAILED DESCRIPTION OF THE INVENTION

PI3K signalling is the most increased pathway in human cancers. The four isoforms of PI3K are thought to be activated by different redundant mechanisms leading to a common downstream signalling. The inventors questioned this concept, by mapping differential isoform-specific downstream signalling in response to their constant selective inhibition in pancreatic cancer, a disease currently without therapy. They identified common and specific signals activated by each PI3K isoform. A complex stimulation of cancer cells enhances the activation of PI3Ks, and allows the isoform-selective activation of other signalling routes, improving the importance of this signal in cancer cell survival; in opposition, in serum deprived condition, these same cells rely for their survival on only one amongst the four PI3K downstream GPCR or RTK. These data make the rational for the development of highly selective PI3K isoform drugs used in combination, instead of compounds inhibiting all PI3Ks. In particular, the inventors showed that combined p110α and p110γ inhibition is the most efficient strategy for pancreatic cancer patients.

Accordingly, the first object of the present invention relates to a method of treating pancreatic cancer in a patient in need thereof comprising administering to the patient a therapeutically effective combination of at least one p110α selective inhibitor and at least one p110γ selective inhibitor.

As used herein the term "pancreatic cancer" or "pancreas cancer" as used herein relates to cancer which is derived from pancreatic cells. In particular, pancreatic cancer included pancreatic adenocarcinoma (e.g., pancreatic ductal adenocarcinoma) as well as other tumors of the exocrine pancreas (e.g., serous cystadenomas), acinar cell cancers, and intraductal papillary mucinous neoplasms (IPMN).

As used herein, the term "treatment" or "treat" refer to both prophylactic or preventive treatment as well as curative or disease modifying treatment, including treatment of subject at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "PI3K" has its general meaning in the art and refers to a phosphoinositide 3-kinase. PI3Ks belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate (PIP2) giving rise to phosphatidylinosito-3,4,5-trisphosphate (PIP3). PIP3 functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99).

As used herein, the term "p110α inhibitor" has its general meaning in the art and refers to an inhibitor of the catalytic subunit p110 of PI3Kα. As used herein, the term "p110γ inhibitor" has its general meaning in the art and refers to an inhibitor of the catalytic subunit p110 of PI3Kγ. As used herein, the term "selective inhibitor" generally refers to a compound that inhibits the activity or expression of the more effectively than at least one other isozyme(s) of the PI3K family. A selective inhibitor compound is therefore more selective than conventional PI3K inhibitors such as wortmannin and LY294002, which are "nonselective PI3K inhibitors. Non-limiting examples of inhibitors include compounds, molecules, chemicals, polypeptides and proteins that inhibit and/or reduce the expression and/or activity of the specific p110 subunit. Additional non-limiting examples of inhibitors include ATP-competitive inhibitors. Further non-limiting examples of inhibitors include ribozymes, antisense oligonucleotides, shRNA molecules and siRNA molecules that specifically inhibit and/or reduce the expression or activity of the specific p110 subunit.

Non-limiting examples of p110α selective inhibitors are disclosed in Schmidt-Kittler et al., Oncotarget (2010) 1(5): 339-348; Wu et al., Med. Chem. Comm. (2012) 3:659-662; Hayakawa et al., Bioorg. Med. Chem. (2007) 15(17): 5837-5844; and PCT Patent Application Nos. WO2013/049581 and WO2012/052745, the contents of which are herein incorporated by reference in their entireties. In particular non-limiting embodiments, the p110α selective inhibitor is derived from imidazopyridine or 2-aminothiazole compounds. Further non-limiting examples include those described in William A Denny (2013) Phosphoinositide 3-kinase a inhibitors: a patent review, Expert Opinion on Therapeutic Patents, 23:7, 789-799. Further non-limiting examples include BYL719, INK-1114, INK-1117, NVP-BYL719, SRX2523, LY294002, PIK-75, PKI-587, A66, CH5132799 and GDC-0032 (taselisib). One inhibitor suitable for the present invention is the compound 5-(2,6-dimorpholin-4-yl-pyrimidin-4-yl)-4-trifluoromethyl-pyridin-2-ylamine that is described in WO2007/084786, which is hereby incorporated by reference in its entirety hereto. Another inhibitor suitable for the present invention is the compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) that is described in WO 2010/029082, which is hereby incorporated by reference in its entirety hereto.

Suitable p110γ selective inhibitors have been described in U.S. Patent Publication Nos. 2004/0092561 A1, 2005/004195 A1, 2005/020631 A1, 2005/020630 A1, 2004/248954 A1, 2004/259926 A1, 2004/0138199 A1, 2004/01219996 A1, and 2004/0248953 A1, and International Patent Publication No. WO 04/029055 A1, the entire disclosures of which are hereby incorporated herein by reference. Further examples of inhibitors include 2-amino-N-[1-(4-chloro-7-ethoxy-2-methyl-2H-indazol-6-yl)ethyl]pyrazolo[1,5-a]pyrimidine-3-carboxamide; 2-amino-N-[1-(4-chloro-7-ethoxy-2-ethyl-2H-indazol-6-yl)ethyl]pyrazolo[1,5-a]pyrimidine-3-carboxamide; 2-amino-N-[1-(4-chloro-7-ethoxy-1H-indazol-6-yl)ethyl]pyrazolo[1,5-a]pyrimidine-3-carboxamide; 2-amino-N-[1-(4-chloro-7-ethoxy-1-methyl-1H-indazol-6-yl)ethyl]pyrazolo[1,5-a]pyrimidine-3-carboxamide; 2-amino-N-{1-[4-chloro-7-ethoxy-1-(2-methoxyethyl)-1H-indazol-6-yl]ethyl}pyrazolo[1,5-a]pyrimidine-3-carboxamide; 2-amino-N-(1-(4-chloro-7-ethoxy-1-(2-hydroxyethyl)-1H-indazol-6-yl)ethyl)pyrazolo[1,5-a]pyrimidine-3-carboxamide; 2-amino-N-(1-(4-chloro-1-(cyanomethyl)-7-ethoxy-1H-indazol-6-yl)ethyl)pyrazolo[1,5-a]pyrimidine-3-carboxamide; 2-amino-N-(1-(1-benzyl-4-chloro-7-ethoxy-1H-indazol-6-yl)ethyl)pyrazolo[1,5-a]pyrimidine-3-carboxamide; 2-amino-N-(1-(4-chloro-7-ethoxy-1-isobutyl-1H-indazol-6-yl)ethyl)pyrazolo[1,5-a]pyrimidine-3-carboxamide; 2-amino-N-(1-(4-chloro-1-cyclobutyl-7-ethoxy-1H-indazol-6-yl)ethyl)pyrazolo[1,5-a]pyrimidine-3-carboxamide; 2-amino-N-(1-(4-chloro-7-ethoxy-1-isopropyl-1H-indazol-6-yl)ethyl)pyrazolo[1,5-a]pyrimidine-3-carboxamide; 2-amino-N-(1-(4-chloro-7-ethoxy-2-(2-methoxyethyl)-2H-indazol-6-yl)ethyl)pyrazolo[1,5-a]pyrimidine-3-carboxamide; 2-amino-N-(1-(4-chloro-7-ethoxy-2-(2-hydroxyethyl)-2H-indazol-6-yl)ethyl)pyrazolo[1,5-a]pyrimidine-3-carboxamide; 2-amino-N-(1-(4-chloro-2-(cyanomethyl)-7-ethoxy-2H-indazol-6-yl)ethyl)pyrazolo[1,5-a]pyrimidine-3-carboxamide; 2-amino-N-(1-(2-benzyl-4-chloro-7-ethoxy-2H-indazol-6-yl)ethyl)pyrazolo[1,5-a]pyrimidine-3-carboxamide; 2-amino-N-(1-(4-chloro-7-ethoxy-2-isobutyl-2H-indazol-6-yl)ethyl)pyrazolo[1,5-a]pyrimidine-3-carboxamide; 2-amino-N-(1-(4-chloro-2-cyclobutyl-7-ethoxy-2H-indazol-6-yl)ethyl)pyrazolo[1,5-a]pyrimidine-3-carboxamide; 2-amino-N-(1-(4-chloro-7-ethoxy-2-isopropyl-2H-indazol-6-yl)ethyl)pyrazolo[1,5-a]pyrimidine-3-carboxamide; 2-amino-N-(1-(2-(2-amino-2-oxoethyl)-4-chloro-7-ethoxy-2H-indazol-6-yl)ethyl)pyrazolo[1,5-a]pyrimidine-3-carboxamide; 2-amino-N-(1-(1-(2-amino-2-oxoethyl)-4-chloro-7-ethoxy-1H-indazol-6-yl)ethyl)pyrazolo[1,5-a]pyrimidine-3-carboxamide; 2-amino-N-(1-(2-(but-2-ynyl)-4-chloro-7-ethoxy-2H-indazol-6-yl)ethyl)pyrazolo[1,5-a]pyrimidine-3-carboxamide; 2-amino-N-(1-(1-(but-2-yn-1-yl)-4-chloro-7-ethoxy-1H-indazol-6-yl)ethyl)pyrazolo[1,5-a]pyrimidine-3-carboxamide; 2-amino-N-(1-(4-chloro-7-phenyl-1H-indazol-6-yl)ethyl)pyrazolo[1,5-a]pyrimidine-3-carboxamide; 2-amino-N-(1-(4-chloro-1-methyl-7-phenyl-1H-indazol-6-yl)ethyl)pyrazolo[1,5-a]pyrimidine-3-carboxamide; 2-amino-N-(1-(4-chloro-2-methyl-7-phenyl-2H-indazol-6-yl)ethyl)pyrazolo[1,5-a]pyrimidine-3-carboxamide; 2-amino-N-(1-(4-chloro-1-((1-methyl-1H-pyrazol-3-yl)methyl)-7-phenyl-1H-indazol-6-yl)ethyl)pyrazolo[1,5-a]pyrimidine-3-carboxamide; 2-amino-N-(1-(4-chloro-2-((1-methyl-1H-pyrazol-3-yl)methyl)-7-phenyl-2H-indazol-6-yl)ethyl)pyrazolo[1,5-a]pyrimidine-3-carboxamide; 2-amino-N-(1-(4 chloro-1-(2-morpholinoethyl)-7-phenyl-1H-indazol-6-yl)ethyl)pyrazolo[1,5-a]pyrimidine-3-carboxamide; 2-amino-N-(1-(4-chloro-2-(2-morpholino-2-oxoethyl)-7-phenyl-2H-indazol-6-yl)ethyl)pyrazolo[1,5-a]pyrimidine-3-carboxamide; 2-amino-N-(1-(2-(2-aminoethyl)-4-chloro-7-phenyl-2H-indazol-6-yl)ethyl)pyrazolo[1,5-a]pyrimidine-3-carboxamide; 2-amino-N-(1-(1-(2-aminoethyl)-4-chloro-7-phenyl-1H-indazol-6-yl)ethyl)pyrazolo[1,5-a]pyrimidine-3-carboxamide; 2-amino-N-(1-(3-bromo-4-chloro-7-phenyl-1H-indazol-6-yl)ethyl)pyrazolo[1,5-a]pyrimidine-3-carboxamide; 2-amino-N-(1-(4-chloro-3-methyl-7-phenyl-1H-indazol-6-yl)ethyl)pyrazolo[1,5-a]pyrimidine-3-carboxamide; 2-amino-N-(1-(3,4-dimethyl-7-phenyl-1H-indazol-6-yl)ethyl)pyrazolo[1,5-a]pyrimidine-3-carboxamide; 2-Amino-N-{1-[8-chloro-5-(3-fluorophenyl)-3-methylimidazo [1,5-a]

pyridin-6-yl]ethyl}pyrazolo[1,5-a]pyrimidine-3-carboxamide; 2-Amino-N-(1-(8-chloro-5-phenylimidazo[1,5-a]pyridin-6-yl)ethyl)pyrazolo[1,5-a]pyrimidine-3-carboxamide; 2-Amino-N-[1-(8-chloro-5-phenylimidazo[1,5-a]pyridin-6-yl)ethyl]pyrazolo[1,5-a]pyrimidine-3-carboxamide; 2-Amino-N-{1-[5-(3-fluorophenyl)-3,8-dimethylimidazo[1,5-a]pyridin-6-yl]ethyl}pyrazolo[1,5-a]pyrimidine-3-carboxamide; 2-Amino-N-[1-(8-cyano-5-phenylimidazo[1,5-a]pyridin-6-yl)ethyl]pyrazolo[1,5-a]pyrimidine-3-carboxamide; or a pharmaceutically acceptable salt thereof As used herein, the term "combination" is intended to refer to all forms of administration that provide a first drug together with a further (second, third . . . ) drug. The drugs may be administered simultaneous, separate or sequential and in any order. Drugs administered in combination have biological activity in the patient to which the drugs are delivered. Within the context of the invention, a combination thus comprises at least two different drugs, and wherein one drug is at least one p110α selective inhibitor and wherein the other drug is at least one p110γ selective inhibitor. In some instance, the combination of the present invention results in the synthetic lethality of the cancer cells.

A "therapeutically effective amount" refers to an amount effective, at dosages and for periods of time necessary, to achieve a desired therapeutic result. A therapeutically effective amount of drug may vary according to factors such as the disease state, age, sex, and weight of the individual, and the ability of drug to elicit a desired response in the individual. A therapeutically effective amount is also one in which any toxic or detrimental effects of the antibody or antibody portion are outweighed by the therapeutically beneficial effects. The efficient dosages and dosage regimens for drug depend on the disease or condition to be treated and may be determined by the persons skilled in the art. A physician having ordinary skill in the art may readily determine and prescribe the effective amount of the pharmaceutical composition required. For example, the physician could start doses of drug employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. A therapeutically effective amount of a therapeutic compound may decrease tumor size, or otherwise ameliorate symptoms in a subject. One of ordinary skill in the art would be able to determine such amounts based on such factors as the patient's size, the severity of the patient's symptoms, and the particular composition or route of administration selected. An exemplary, non-limiting range for a therapeutically effective amount of drug is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. An exemplary, non-limiting range for a therapeutically effective amount of an antibody of the present invention is 0.02-100 mg/kg, such as about 0.02-30 mg/kg, such as about 0.05-10 mg/kg or 0.1-3 mg/kg, for example about 0.5-2 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the efficacy of the treatment is monitored during the therapy, e.g. at predefined points in time. As non-limiting examples, treatment according to the present invention may be provided as a daily dosage of the agent of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

Typically, the drugs of the present invention are administered to the patient in the form of a pharmaceutical composition which comprises a pharmaceutically acceptable carrier. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. For use in administration to a subject, the composition will be formulated for administration to the patient. The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques. Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added. Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be effected in a rectal suppository formulation (see above) or in a suitable enema formulation. Patches may also be used. The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. For example, an antibody present in a pharmaceutical composition of this invention can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 1 mg/m$^2$ and 500 mg/m$^2$. However, it will be appreciated that these schedules are exemplary and that an optimal schedule and regimen can be adapted taking into account the affinity and tolerability of the particular antibody in the pharmaceutical composition that must be determined in clinical trials. A pharmaceutical composition of the invention for injection (e.g., intramuscular, i.v.) could be prepared to contain sterile buffered water (e.g. 1 ml for intramuscular), and between about 1 ng to about 100 mg, e.g. about 50 ng to about 30 mg or more preferably, about 5 mg to about 25 mg, of the inhibitor of the invention.

The invention will be further illustrated by the following figures and examples. However, these examples and figures should not be interpreted in any way as limiting the scope of the present invention.

FIGURES

FIG. 1: Combination of p110γ and p110α inhibitors lead to synergistic proliferation inhibition associated a loss of pAkt (S473)

A-C) Dose-response of three human pancreatic primary organoids viability were evaluated by CellGlo Titer assay after 5 days in complete medium (NFMm) with or without PI3K inhibitors, as indicated (n≥3).

D) Evaluation of synergistic action on survival of 7 human pancreatic cancer cells cultured in 2D (Capan-1, BxPC-3, Panc-1 and MIA PaCa-2) and 3D (B20, B24 and B34) was performed determined using CompuSyn software [49] based on the quantitative analysis of dose-effect relationships on multiple drugs. Combinational index (CI) values were calculated to confirm synergy. CI<1 indicates synergistic effects, 0.8≥CI≤1.2 indicates the mean additive effect of the drugs, and CI>1 represents an antagonistic effect.

FIG. 2: Synergistic action of p110α and p110γ is specific to these two isoforms for their effect on cell survival and down-regulation of pAkt.

A-D) Survival of four human pancreatic cancer cells treated during 6 days by p110γ inhibitor with or without isoform-selective inhibitor was assessed by MTT assay (n≥4).

EXAMPLE

Material & Methods
Reagents
Reagents were purchased as follows: pan-PI3K and isoform-selective PI3K inhibitors from Axon Medchem; Gemcitabine was a kind gift of hospital (IUCT-O, France); EGF (236-EG-200) was from R&D Systems; LPA (BML-LP100-0005) and S1P (BML-SL140-0001) were from Enzo Life Sciences; PDGF-BB (#100-14B) and IGF-1 (#100-11) were from PreproTech; MTT was from Euromedex (4022); Caerulein (C9026), Gallein (G1137), Pertussis toxin (P2980), Glucose (G6152), Insulin (91077C), MEM amino acids solution (M5550), Hank's balanced salt solution (H8264), RPMI-1640medium without glucose (R1383) were from Sigma. All PI3K inhibitors were resuspended in DMSO, corresponding at the vehicule in experiences. All products were resuspended according to the supplier's instructions.

Cell Lines and Tissue Samples
Human pancreatic ductal cell lines (HPNE, HPNE hTERT and HPDE) were a kind gift from Tsao MS (Toronto, Canada); human pancreatic cell lines (Capan-1, BxPC-3, PANC-1, MIA PaCa-2) came from American Type Culture Collection (ATCC), human acute myeloid leukemia cell line (MOLM4) was a kind gift from Jean-Emmanuel Sarry (CRCT, France) and murine pancreatic cancer cell lines (DT4994, DT6585, DT6606, DT8442, DT8661, R221, R259) were a kind gift from Dieter Saur (Klinikum rechts der Isar der TU Munchen, Germany). Patient organoid cell cultures were obtained by Maximilian Reichert (Klinikum rechts der Isar der TU Munchen, Germany) collected during surgery. Human normal and adenocarcinoma pancreatic samples (>30% tumoral cells) were selected by A Brouchet-Gomez, and collected according French and European legislation (CRB, France). Murine pancreas samples were obtained from LSL-Kras$^{G12D}$; Pdxl-Cre (named KC) and Pdxl-Cre or p110α$^{+/lox}$ (named WT) treated or not with Caerulein to mimic inflammation [39]. Genetic alterations and patient survival curve were performed with TGCA data on cBioPortal web site (cbioportal.org).

In Vitro Culture of Pancreatic Cell Lines

Primary human cells derived from the ducts of the pancreas transduced with an hTERT cDNA, HPNE [40], and transformed with Kras, HPNE Kras [41] were cultured in 25% Medium M3 base (M300F-500, Incell), 75% DMEM without glucose (D5030, Sigma), 2 mM Glutamine (G7513, Sigma), 1.5 g/L sodium bicarbonate (S5761, Sigma), 5% FBS (Gibco), 10 ng/ml EGF (236-EG-200, R&D Systems) and 5.5 mM Glucose (G6152, Sigma). Human Pancreatic duct epithelial cell line HPDE [42] was cultured with Keratinocyte serum-free medium (10724-011, Gibco) supplemented with 0.2 ng/ml EGF and 30 µg Extract pituitary extract bovine (P1476, SIGMA). Human pancreatic cancer cell lines Capan-1 and BxPC-3 were cultured in RMPI 1640 medium. PANC-1, MIA PaCa-2 and all murine pancreatic cancer cells were cultured in Dulbecco's Modified Eagle's Medium with 4.5 g of glucose (D6429, Sigma). All media were supplemented with 10% fetal bovine serum (Eurobio), 1% glutamin (G7513, Sigma) and 1% antibiotics (penicillin/streptomycin, P0781, Sigma). Patient's organoids cell lines were cultured in special medium (Reichert composition, article in preparation). Cells were grown in a humidified incubator at 37° C., 5% CO2. Mycoplasmic free-state was controlled by PCR.

Vector Construction and Pancreatic Cancer Cell Transduction pLVTHM was kindly provided by B. Couderc the Cancer Research Center of Toulouse (France) and digested with Cla1/Mlu1. The sequence encoding shp110α1, shp110α2, shp110γ1, shp110α2 or shSCR2 was inserted in digested pLVTHM. Resultant plasmids were checked by sequencing.

Briefly, 5·10$^4$ Capan-1 cells were plated in 8-well plates. After 24 h, they were transduced overnight (20 h) with 1 ml of lentiviral vector and 4 µl of hexadimethrine bromide, grown and selected for efficient transduction with the lentivector using cell sorting on positive GFP expression.

RNA Interference

Capan-1 were transfected with siRNA targeting p110α (L-003018-00, SMARTpools, Dharmacon, 20 nM), p110γ (L-005274-00, SMARTpools, Dharmacon, 20 nM), or non-targeting control pool (D-001810-10, SMARTpools, Dharmacon, 20 nM) using Lipofectamine 2000 (11668, Invitrogen) in Opti-MEM medium (Ser. No. 11/058,021, Invitrogen), according to the reverse transfection Invitrogen's instructions.

Pancreatic Cancer Cell Treatment for Western Blot Analysis

Pancreatic cancer cell were cultured consistent conditions. Eight hours after plating of cells, they were serum-starved during 16 h, over-night. Cells were pre-treated with inhibitors or their accordingly diluted vehicle (DMSO) during 1 h, then stimulated or not for 10 min or 24 h with 2% FBS, for 10 min with 20 µg/ml EGF, 100 nM Insulin, 50 ng/ml IGF-1, 1 µM LPA, 30 ng/ml PDGF, 200 nM S1P, 1× amino acids or 2 g/l glucose.

Western Blot Analysis

Cells were harvested on ice, washed twice with cold PBS, collected, and frozen at −80° C. Dry pellets of cells were lysed in 50 mM Tris-HCl, pH 7.5, 150 mM NaCl, 1 mM EDTA, 1% Triton-X100 (X100, Sigma) supplemented with protease and phosphatase inhibitors (sodium orthovanadate (S6508, Sigma), 1 mM DTT, 2 mM NaF (S1504, Sigma) and cOMPLETE Mini Protease Inhibitor Cocktail (ROCHE). Protein concentration was measured using BCA Protein Assay kit (Interchim), and equal amounts of proteins were subjected to SDS-PAGE and transferred onto nitrocellulose membrane (BioTraceNT, Pall Corp). Membranes were washed in Tris Buffered Saline supplemented with 0.1% Tween-20 (TBS-T) then saturated in TBS-T with 5% non-fat dry milk, incubated overnight with primary antibodies in TBS-T with 5% BSA, washed and revealed according to Cell Signaling Technology protocol.

RT-qPCR Analyses

Cells were harvested on ice, washed twice with cold PBS, collected, and frozen at 80° C. RNA of cell pellets was isolated according TRIzol protocol (Life Technologies). RT-qPCR reactions were carried out using RevertAid H Minus Reverse Transcriptase (#EP0452, Thermo Fisher) with Random hexamer (#SO142, Thermo Fisher) and Sso-Fast EvaGreen Supermix (#172-5211, Bio-Rad) according to the manufacturers' instructions. The selected primers were designed to amplify short fragments (60 to 103 bp) in order to obtain optimal PCR efficiency between 85 and 115% efficiency. qPCR data were normalized with GAPDH and analysed on Livak's instructions (2(−Delta Delta C(T)) method [43]).

Viability Assays

Pancreatic cancer cells cultured in 2D were seeded in 96-well plates, 5 000 cells per well. After their adhesion (24 h), cells were treated and stimulated or not with 2% FBS, 2% heading FBS, 20 µg/ml EGF, 100 nM Insulin, 50 ng/ml IGF-1, 1 µM LPA, 30 ng/ml PDGF, 200 nM S1P, 1× amino acids or 2 g/l glucose. MTT 3-(4,5-dimethyl-2-thiazol)-2,5-diphenyl-2H-tetrazolium bromide (4022, Euromedex) was added to each well at 500 µg/mL for 2 hours at 37° C. After removing medium with MTT, 100 µl of dimethylsulfoxide (DMSO) were added for 1 h to each well at 37° C. Viability was estimated by measuring absorbance at 570 nm on Mithras LB 940 plate reader (Berthold Technologies). Cell viability of pancreatic cancer cell cultured in 3D (organoids) was determined using the CellTiter Glo® luminescent cell viability assay kit (Promega). Briefly, 1×10$^3$ cells were seeded per well in 96-well plates and incubated overnight (18 h). After 5 days of treatment with drugs, cells were incubated in 100 µL CellTiter Glo reagent for 30 min with orbital agitation, then signals were measured on a FLUOstar Omega microplate luminometer (BMG Labtech). All plates, MTT and CellTiter Glo assays, have blank wells containing cell-free medium to measure background DO and luminescence.

Proliferation Assays

Proliferation of established cell lines was assessed by cell counting (Cellometer Mini, Ozyme) with 0.1×10$^6$ cells per well in six-well plates. Proliferation was also assessed by BrdU assay. Cells were seeded 2×10$^3$ cell per well in 96-well plate. After treatment, cells were incubated 4 h at 37° C. with 10 µl BdrU per well (1×, #6813, Cell Signaling). BrdU incorporation was estimated by measuring absorbance at 450 nm on Mithras LB 940 plate reader (Berthold Technologies) according to Cell Signaling Technology protocol.

DEVD Cleavage Enzyme Assay

Protein lysates were incubated for 2 h at 37° C. with 3 mg/ml of Ac-Asp-Glu-Val-Asp-pNA (pNA=p-Nitroaniline) (Enzo Life Sciences). Amount of the released chromophore fluorescent product was determined by spectrometry at 405 nm for the emission wavelength.

Flow Cytometry

Cells were seeded at the concentration of $0.2 \times 10^6$ (short term treatment) or $2 \times 10^6$ (long term treatment) in 10 cm-diameter dish. After 24 h, cells were washed, serum-starved during 16 h and treated during 10 min, 24 h or 9 days with or without 2% FBS. Medium with drug was changed every 48 h. DNA content was evaluated by flow cytometry after fixing, permeabilizing and cell labeling with ethanol 70% and propidium iodide (25 µg/mL, P3566, Invivogen) for 30 min at 37° C. in the dark using a FACScan cytometer (MACSQuant VYB, Miltenyi Biotec).

Soft Agar Colony Formation Assay

Wells were coated with 2 ml per well of 0.6% low-melt agarose (A7002, Sigma). Capan-1 cells ($2 \times 10^4$) were resuspended in 1.0 mL of RPMI medium containing 0.3% low-melt agarose, 10% fetal bovine serum (Gibco), 1% of penicillin-streptomycin and 1% of glutamine. The cell mixture was plated on top of 0.6% agarose solidified layer. Plates were incubated for 2 weeks at 37° C. in 5% CO2 in humidified incubator. Pictures of all conditions were taken Axiovert microscope (Zeiss).

Organoids and Soft Agar Colonies Quantification

Pictures of organoids were taken with the same objectif (×4) with UTVIX-2 microscope (Olympus). Size and numbers of organoids and soft area colonies were evaluated with Fiji (Fiji Is Just ImageJ) by created plugin allowing us to automate quantification.

Details of this procedure for organoids quantification are:
run("8-bit");
run("Subtract Background . . . ", "rolling=20 light");
setAutoThreshold("Default");
//run("Threshold . . . ");
setThreshold(0, 230);
setOption("BlackBackground", false);
run("Convert to Mask");
run("Dilate");
run("Fill Holes");
run("Convert to Mask");
run("Set Measurements . . . ", "area mean limit display redirect=None decimal=3");
run("Analyze Particles . . . ", "size=200-Infinity pixel show=Outlines display clear include summarize");

Details of this procedure for soft agar colonies quantification are:
run("8-bit");
setAutoThreshold("Default");
//run("Threshold . . . ");
setThreshold(145, 255);
setOption("BlackBackground", false);
run("Convert to Mask");
run("Dilate");
run("Dilate");
run("Fill Holes");
run("Convert to Mask");
run("Set Measurements . . . ", "area mean limit display redirect=None decimal=3");
run("Analyze Particles . . . ", "size=200-Infinity pixel show=Outlines display clear include summarize");
run("Close");

SILAC Labelling of Capan-1 Cell Line

SILAC RPMI medium deficient in L-Lysine and L-Arginine (Fisher Scientific, 1214-2410) was supplemented with 10% dialyzed FBS (Gibco, 26400-044), 1% glutamine (Sigma, G7513-100ML), 1% penicillin/streptomycin (Lonza, 17-605E), and 0.01% plasmocin, and aminoacids: 100 mg/L L-Proline (ULM-8333), 242 mg/L L-Arginine and 40 mg/L L-Lysine. All aminoacids were supplied by Cambridge Isotope Laboratories. For heavy labelling, aminoacids used were the following: L-Arginine-$^{13}C_6$-$^{15}N_4$ hydrochloride (Arg+10 Da) (CNLM-539-H) and L-Lysine-$^{13}C_6$-$^{15}N_2$ dihydrochloride (Lys+8 Da) (CNLM-291-H), whereas in light medium, L-Arginine-$^{12}C_6$-$^{14}N_4$ hydrochloride (ULM-8347) and L-Lysine-$^{12}C_6$-$^{14}N_2$ dihydrochloride (ULM-8766) were added in basal SILAC medium. After 6 passages with respective labelling media (21 days of culture), incorporation of heavy aminoacids was found >95% (as determined by LC-MS/MS—data not shown). No isotopic arginine/proline conversion was observed. Capan-1 cells cultured in heavy or light SILAC media did show any morphological and proliferation changes compared to cells cultured in standard medium (data not shown).

SILAC Cell Treatment

Light amino acid-labelled and heavy amino acid-labelled Capan-1 cells (respectively called thereafter "light" and "heavy" cells) were washed twice with phosphate buffer saline (PBS; SIGMA; D8537), trypsined (GE Healthcare; L11-002) and plated at a concentration of $2.5.10^6$ cells in a 14.4 cm-diameter dish (Dutscher, 055063). After 48 h, cells were serum-starved during 16 h, over-night. Light and heavy cells were pre-treated respectively with inhibitors or their accordingly diluted vehicle (DMSO) during 1 h, then stimulated or not for 10 min or 24 h with 2% dialysed FBS. After 10 min and 24 h of FBS stimulation, heavy cells and light cells were maintained on ice, washed three times with cold PBS and lysed.

Four biological replicates were sampled for each time point. These biological replicates were performed on four weeks.

SILAC Sample Preparation

Cells were lysed on the plate with 2 mL of lysis buffer (Tris-HCl 100 mM-pH 7.8 (Sigma, T1503), SDS 1% (Sigma, L3771), EDTA 5 mM-pH7.8 (Euromedex, EU-0007-B), proteases and phosphatases inhibitors (Sigma) containing 1× cOmplete Roche proteases inhibitors cocktail (SIGMA, 04693132001), NaF 10 mM (Sigma, S1504), NaPPi 10 mM (Sigma, S6422) and $Na_3VO_4$ 10 mM (Sigma, 450243)) during 30 min at 4° C. in dark. Cells were scraped, harvested and incubated 20 min at 57° C. To eliminate DNA-dependent viscosity, samples were sonicated (amplitude 40%, pulse 1 sec, interval 1 sec during 60 sec). Three other lysis buffers were also tested (Buffer 1: $NH_4HCO_3$ 100 mM pH7.8, Urea 8M; Buffer 2: Tris-HCl 100 mM pH7.8, Urea 8M; Buffer 3/RIPA: Tris-HCl50 mM, NaCl 150 mM, Nonidet P-40 1% pH 7.8, SDS 0.1% (w/v)); the chosen buffer allowed the better extraction of phospho-tyrosine proteins as assessed by Western blotting with anti-pY (p-Tyr100) antibody (Cell Signaling Technology; 8954S) as compared to in gel 1-DE profile. Cell lysates were then cleared from insoluble fraction by centrifugation at 10,000×g for 15 min at 25° C., and protein concentration was measured by 2-D Quant kit (GE Healthcare, 80-6483-56). For each biological replicate, light and heavy lysates were mixed at a 1:1 ratio for a total amount of 6 mg.

Protein samples were reduced with 100 mM DTT (Sigma, D9163) for 35 min at 57° C. and then handled according to the FASP (Filter Aided Sample Preparation) digestion protocol [44] using Amicon Ultra-15 Centrifugal Filter device (10 kDa cut-off, MILLIPORE, UFC901096). The $1^{st}$ step consisted in the replacement of SDS by urea, then a dilution with UA buffer (Tris-HCl100 mM-pH 8.5, Urea 8M (Sigma, U5128)) and an alkylation with CAA solution (Tris-HCl 100 mM pH 8.5, Urea 8M, Chloroacetamide 50 mM (Sigma, CO267)). For optimization of trypsin efficiency, urea concentration was decreased at 200 mM with Ammonium Bicarbonate buffer ($NH_4HCO_3$ 0.05M (SIGMA, 09830) and 10 mM phosphatase inhibitors as previously used in lysis buffer). In a $2^{nd}$ step, Trypsin (Promega, V5117) digestion was performed at 1:50 (w/w) trypsin:protein ratio overnight at 37° C. on the Amicon Ultra-15 Centrifugal Filter. Tryptic peptides were acidified with 1% trifluoroacetic acid (TFA—Sigma, T6508), cleared at 5,000 rpm for 15 minutes at 15° C., and desalted using C18 Sep-Pak plus cartridges (Waters, WAT043395, 500 mg sorbent). Resin was conditioned with 15 mL in 80% Acetonitrile (ACN—Sigma, 34888) then equilibrated with 15 mL in 0.1% TFA. After the loading step, sample was washed with 15 mL in 0.1% TFA, and the elution was performed with 4 mL in 80% ACN, 0.1% TFA). Eluted peptides were lyophilized with a speed-vacuum over night.

Protocol for the enrichment with $TiO_2$ beads is based on Larsen et al., [45] and Jensen et al. [46]. In details, dried peptide pellets were resuspended in 1 ml of Titansphere $TiO_2$ blocking buffer (80% ACN, 0.1% TFA, 20 mg/mL Glycolic acid (Sigma, 149357), loaded onto eppendorf tube containing $TiO_2$ using a $Tio_2$ beads/peptides ratio equal to 4, w/w (i.e. 6 mg of peptides for 24 mg of $TiO_2$ beads (GL Sciences Inc, $TiO_2$ NP 100A 5 µm, 5020-75000)) and incubated 45 min at room temperature under agitation. In advance, the $TiO_2$ beads were washed twice with 2 ml of 0.5% $NH_4OH$ (SIGMA, 338818), 40% ACN pH5 (first washing) and 2 ml of 80% ACN, 0.1% TFA (second washing), and were incubated with blocking buffer. The bound peptides were eluted twice with 400 µl elution buffer (0.5% $NH_4OH$, 4% ACN pH 10.5). To eliminate residual beads, the $TiO_2$ eluates were injected on C8 columns (Dyneon/3M, Empore Cartridge C8-SD 4MM/1ML, 1 cc Standard Density, 4114SD), then eluted with 400 µl of 80% ACN, 1% TFA, and were finally splitted in two fractions (10% of the volume was used for $TiO_2$ enrichment fraction-and 90% for phosphotyrosine enrichment, as described hereafter) and were dried with a speed-vacuum. During optimization steps, 20 mg/mL lactic acid (Sigma, 69785), and 20 mg/mL Glycolic acid (Sigma, 124737), and 5 mg/mL DHB were compared for their ability to give the best enrichment of phosphopeptides over total peptides, according to Ayral UK and al., [47]; Glycolic acid was finally chosen as the best blocking agent.

Phospho-Tyrosine enrichment was performed as recommended by the supplier (PTMScan Phospho-Tyrosine Mouse mAb (P-Tyr-100) (Cell Signalling Technology, #5636)). $TiO_2$ enriched dried peptides pellets were resuspended in 350 µl of IAP buffer (50 mM MOPS/NaOH, 10 mM $Na_2HPO_4$, 50 mM NaCl pH 7.2-7.4 (Sigma, M9381, 255793, S9888)), sonicated and pH was controlled (neutral pH 6). After four washing of beads with 1×PBS, 5.4 mg of TiO2-enriched peptides were incubated with 18 µl of beads over-night at 4° C. under agitation (Cell Signalling Technology, PTMScan® Phospho-Tyrosine Rabbit mAb (P-Tyr-1000) Kit, #8803S). After 1 min of 2700 g centrifugation, the supernatant (flowthrough, FT) was removed. Phosphotyrosine peptides were eluted twice with 100 µl of 0.15% Trifluoroacetic acid (TFA, Sigma, T6508), the two eluates were combined and the resulting sample was dried in a speed-Vac.

Data-Dependent Acquisition LC-MS/MS

SILAC samples ($TiO_2$ enriched peptides and flowthrough peptides) were resuspended with 2% acetonitrile, 0.05% TFA and analyzed by nano-LC-MS/MS using an UltiMate 3000 system (Dionex) coupled to LTQ-Orbitrap Velos mass spectrometers (Thermo Fisher Scientific, Bremen, Germany). Five microliters of each peptide sample were loaded on a C18 precolumn (300 µm inner diameter×5 mm; Dionex) at 20 µl/min in 5% acetonitrile, 0.05% trifluoroacetic acid. After 5 min of desalting, the precolumn was switched online with the analytical C18 column (75 µm inner diameter×50 cm; in-house packed) equilibrated in 95% solvent A (5% acetonitrile, 0.2% formic acid) and 5% solvent B (80% acetonitrile, 0.2% formic acid). Peptides were eluted using a 5-50% gradient of solvent B during 310 min at a 300 nl/min flow rate. The LTQ-Orbitrap was operated in data-dependent acquisition mode with the Xcalibur software. Survey scan MS spectra were acquired in the Orbitrap on the 350-1,800 m/z range with the resolution set to a value of 60,000. The twenty (LTQ-Orbitrap Velos) most intense ions per survey scan were selected for CID fragmentation, and the resulting fragments were analyzed in the linear trap (LTQ). Dynamic exclusion was used within 60 s to prevent repetitive selection of the same peptide.

For peptide identification, raw data files were processed in Proteome Discover 1.4.1.14 (Thermo Scientific) and searched against SwissProt human fasta database of Mascot (2014-06, sprot 20140428.fasta, 542782 sequences, high and medium confidence, Q-value=0.5-0.1). Searches were performed with a precursor mass tolerance set to 5 ppm, fragment mass tolerance set to 0.6 Da and a maximum number of missed cleavages set to 2. Static modifications was limited to carbamidomethylation of cysteine, oxidation of methionine, acetylation of N-term protein, phosphorylations of serine, threonine and tyrosine residues, isotopomeric labelled lysine (+8.014199 Da) and isotopomeric labeled arginine (+10.008269 Da+8.014199 Da). Peptides were further filtered using Mascot significance threshold S/N=1.5 and a FDR<0.01 based on q-Value (Percolator). Phospho-site localization probabilities were calculated with phosphoRS 3.1 (maximum PTMs per peptide 10, maximum position isoforms 200).

Phosphoproteomic Data Analysis

Phosphopeptides filtered with Proteome Discoverer 1.4.1.14 (see criteria above) were isolated from peptides. Median of all median of heavy area was calculated to determine a normalising factor between each biological replicates at the two time of treatment (correction factor=median divided by median of all median). Indeed median of heavy samples (starved untreated cells) across all time and biological replicates is not statistically changed and only 209 phosphopeptides (5%) on 4043 were found significantly variant. Light and heavy areas were further converted in normalised areas allowing statistical comparisons across all conditions at once. Phosphopeptides simultaneously identified and quantified in heavy and light conditions (script in C language), were organised in a list of unique common phosphopeptides in all conditions at 10 min and 24 h and were selected for analysis. Ratios of normalised Light area/normalised Heavy area for each replicates and conditions were centred on FBS/NT condition for identification of phosphopeptides which quantity is varying in a given condition as compared to stimulated FBS condition (centred FBS+inhibitor/NT≥1.4 or ≤0.7). Phosphopeptides which quantities were unchanged were identified. Only the ratios which were changed above and below the thresholds were processed for further analysis. Then, values were centred in line to the highest value for each phosphopeptide. Principle component analysis (PCA, XLSTAT module of excel, ascendant hierarchical clustering with Euclidian distance and Ward's method) was applied. A binary matrix allowed us to allocate these classes of ratios as decreased, increased in each condition if its FBS/NT-centred value was ≥1.4 or ≤0.7. Data representations were performed with bioinformatics tools: Venn diagrams (bioinformatics.psb.ugent.be) and PCA (XLSTAT, excel module, version 2017.4, Addinsoft, USA). Biological functions enrichment was collected with AutoCompare ZE software [48] updated in april 2017 with 14637 biological functions from MSigDB version 6.0 (software.broadinstitute.org/gsea/msigdb), 1893 biological functions from Reactome (reactome.org). Comparison of results between all conditions was performed by nwCompare-Julia (Pont F and al., Proteomics, 2010, sites.google.com/site/fredsoftwares/products/nwcompare--julia). Software called "FindPTM" has been developed to localize phosphates or any other post traductionnal modifications (PTM) positions in proteins sequences starting from the PTMs positions in peptides sequences and the proteins accession numbers. FindPTM align peptides sequences on their corresponding proteins sequences and calculates the PTMs positions on the proteins sequences. FindPTM can process an unlimited number of peptides in an unlimited number of files at a rate of more than 3000 peptides/sec on a Core\texttrademark i7 processor. FinPTM is compatible with Uniprot fasta files. FindPTM output is directly compatible with KEA2 software for phosphosites analysis. The software is free software released under the GNU General Public License (gnu.org/licenses) and available at: sites.google.com/site/fredsoftwares/products/findptm. Empirical kinases were determined using Kinase Enrichment Analysis 2 (KEA2) online software (maayanlab.net/KEA2/).

Statistics

Correlation between proliferation/survival effect and phospho-protein/protein expression levels were obtained by a principal component analysis (PCA) and the calculation of a Pearson r correlation factor, respectively with XLSTAT (version 2017.4, Addinsoft, USA) and GraphPad.

The median dose effect or half the maximal inhibitory concentration (IC50) values for each cell line at different time points were determined using CompuSyn software [49] based on the quantitative analysis of dose-effect relationships on multiple drugs or enzyme inhibitors by Chou and Talalay [50]. Combinational index (CI) values were calculated to confirm synergy. CI<1 indicates synergistic effects, CI=1 indicates the mean additive effect of the drugs, and CI>1 represents an antagonistic effect.

Experimental data provided at least three biological replicates. Statistically significant differences were performed with GraphPad Prism using the T-tests (paired test): * P<0.05,  P<0.01, * P<0.001. Non-significant (ns) if P>0.05.

Results

Conditions of Identification of PI3K Isoform-Specific Adaptative Response

In pancreatic cancer, PI3K signalling is associated with a poor prognosis. Analysis of pS473, pT308 Akt in 11 cancer cell enriched pancreatic cancer samples showed a significant increase in all PDAC tissues as compared to normal adjacent pancreas. However, this was not always coupled to a significant increase in the phosphorylation levels of canonical targets, pPRAS40 or pS6K, in all patients (data not shown), emphasizing the importance of other signalling targets downstream PI3Ks. Long-term inhibition of a core signal node is believed to induce an adaptative modification of the entire signal network. We tested if long-term inhibition of each PI3K isoforms induces a differential change in pancreatic cancer cell adaptation. To answer this question, we devise a strategy to globally identify this adaptive response focusing on phospho-site regulated signalling pathways (data not shown). Amongst the 4 isoforms responsible for the production of PIP3 and Akt activation, the isoforms p110α and p110γ, are identified by us and others to be involved in pancreatic cancerogenesis [18, 19]. The human pancreatic cancer cell line Capan-1 is representative of common genetic alterations found in PDAC (where mutation of Kras is found at 95%, mutation of p53 at 50%, amplification of AKT2 at 6%, amplification of PTEN at 4% [20]) (data not shown). Serum, which consist of a combination of RTK and GPCR stimuli mimicking physiopathological signalling, induces after 10 min a significant activation of class I PI3Ks as assessed by the phosphorylation of Akt and known downstream effectors PRAS40, S6K, S6 (data not shown). Pan-PI3K-targeting inhibitors that inhibit all PI3K isoform (here, LY-294002) completely abolish pAkt and all downstream signals (data not shown). Isoform-selective drugs targeting either p110α (α-inh, A66) or p110β (β-inh, TGX-221), p110γ (γ-inh, AS-252424) significantly inhibited pS473 and pT308Akt levels after 10 min stimulation. α-inh and γ-inh respectively inhibited RTK-driven (EGF) or GPCR-driven (LPA) short-term phosphorylation of Akt (data not shown). A 10 min-targeting of all PI3K, or p110α, p110β, p110γ alone, but not p110δ lead to a significant decrease of pAkt and pPRAS40 levels demonstrating the activation of these three PI3K isoforms upon serum stimulation. PI3K inhibitors are still efficient to inhibit pAkt when diluted 24 h in cell medium (data not shown). We thus chose these stimulation conditions to identify differential phosphoproteome across time in response to three PI3K isoform-selective drugs after SILAC metabolic labelling and enrichment in trypsine-based phosphopeptides by $TiO_2$ beads allowing a robust S/T/Y phosphorylation quantification of thousands of proteins.

Strategy of the Phosphoproteomic Approach in Pancreatic Cancer

We devised a spike-in SILAC [21], where we compare all the treatments with heavy labelled untreated cells (data not shown). Incorporation of heavy isotopes was verified by LC-MS/MS after 6 passages (data not shown); this heavy isotope labelling did not change the properties of Capan-1 cell lines (data not shown). We chose to run 4 experimental replicates at two time points 10 min, 24 h in 5 conditions (untreated, serum, serum+pan-PI3K targeting drug, serum+p110α-targeting drug, serum+p110β targeting drug, serum+p110γ targeting drug), allowing statistical analysis of our data. We performed a normalization of all heavy and light areas to the median of each sample, and a centring in column in comparison to FBS/NT ratio. Heavy/light phospho-peptides ratio above or below 1.4/0.7 in at least one condition were selected and the list of modified phosphopeptide ratios for each condition in a time point were then subjected to statistical analysis, namely a principal component analysis and an hierarchical ascendant clustering. All conditions combined, 3600 heavy/light phosphopeptide ratios were identified and quantified by each comparison (data not shown). Amongst these, 79% serine-sites (S), 19% threonine-sites (T), 2% tyrosine-sites (Y) (data not shown) were quantified; these percentages were unchanged upon PI3K inhibition (data not shown). 10 min- and 24 h-serum stimulation induced a modification of phosphopeptides ratios in 557 and 619 phosphopeptides (corresponding to 28 and 32.1% of all identified peptides—data not shown).

Identification of the Phosphoproteome Specifically Regulated by p110α-, p110β-and p110γ- and all PI3Ks in Pancreatic Cancer Cells We then analyzed the phosphoproteome evolution upon PI3K isoform selective inhibition. Levels of a known PI3K target PRAS40 were changed in similar manner when quantified by LC-MS/MS or by WB (data not shown), validating the phosphoproteomics analysis. p110α-selective inhibitor changed 449 and 404 of serum-induced phosphopeptides at 10 min and 24 h respectively, while p110γ-inhibitor increased and decreased 504 and 404 phosphopeptides, p110β-inhibitor 436 and 437 phosphopeptides at 10 min and 24 h respectively. Interestingly, pan-PI3K inhibitor led to a decreased number of changes at 24 h (427 and 258 phosphopeptides, at 10 min and 24 h, respectively) (data not shown).

PCA analysis demonstrated that at 10 min inhibition, p110β-inh, p110γ-inh and FBS conditions cluster together while inhibition of all PI3Ks or of p110α-only clusters in another group (data not shown); common downstream signalling include 116 phosphoproteins implicated mainly in mRNA splicing, signalling by TGFβ Receptor and gene expression pathways (data not shown). We were able to identify selectively changed phosphopeptides in all conditions tested (data not shown). At 24 h, however, all inhibitors treatment were dissociated from FBS condition, demonstrating the time necessary to induce significant isoform selective changes in signalling networks upon long-term PI3K inhibition (data not shown). Surprisingly, inhibition of all PI3Ks clustered with the inhibition of p110β, while inhibition of p110γ and p110α led to similar abundance modifications of phosphoproteome.

The clustering of changed phosphopeptide ratios identified at both 10 min and 24 h showed isoform-selectivity in PI3K-regulated phosphoproteome, and identified groups of phosphopeptides that were specifically regulated by each isoform-selective drugs or pan-PI3K drug (data not shown). A STRING representation of interaction of identified clusters clearly show a common core regulated by all PI3Ks independently of the used PI3K inhibitor (data not shown). Our data demonstrate that inhibiting all PI3K or one isoform did not induce a similar modification of phosphorylation-regulated proteome already at 10 min of treatment, despite having similar action on the phosphorylation of Akt and PRAS40 (data not shown). An analysis of the functions regulated by the isoform-selective or all-PI3K common peptides showed at 10 min an indistinct global pathways (Reactome), molecular functions and component cellular (Gene Ontology) in all conditions (data not shown). At 24 h, surprisingly, p110γ inhibition led to an increased number of changes in phosphopeptides involved in similar functions and cellular components that those changed by all PI3Ks (data not shown). These data also show that an efficient p110γ regulates similar functions than all PI3Ks, while increasing the number of significantly regulated targets in these functions suggesting that inhibiting p110γ is the most efficient way to inhibit the core PI3K signalling in pancreatic cancer cells. Inhibition of p110γ only could be sufficient to prevent pancreatic cancer cell survival.

Pancreatic Cancer Cells are Sensitive to p110γ Inhibitors and Present Increased Levels of p110γ Expression We next analysed the expression levels of PI3K isoforms in human pancreatic cancer samples by WB. We observed that p110β levels were high but constant, while p110α, p110γ and p110δ protein levels were significantly increased compared to normal adjacent pancreas (data not shown). In human and murine cell lines, p110γ was found significantly increased in two out of four and in three out of seven murine syngenic pancreatic cancer cell lines (data not shown). In serum-starved condition, cell numbers of all human pancreatic cancer cell lines were significantly decreased in time upon p110γ inhibition, regardless p110γ mRNA level of expression (data not shown). p110γ inhibition was almost as effective or more effective that pan-PI3K inhibition. However, they were also sensitive to p110α-inhibition in particular after 9 days of treatment (data not shown). Without serum, inhibiting only one isoform, either p110γ or p110α was sufficient to significantly decrease pancreatic cancer cell numbers, and had similar action than inhibiting all PI3Ks with pan-PI3K inhibitor. Serum stimulation, however, decreased the action of PI3K inhibitors (data not shown), none of them being able to decrease pancreatic cancer cell numbers upon 9 days of treatment. In serum conditions, shRNA targeting either p110a or p110γ partially reduced their anchorage-independent growth in soft agar, confirming the action of pharmacological inhibitors (data not shown). While we observe a significant decrease in pAkt in serum-stimulated condition, serum stimulation prevents the efficiency of PI3K inhibitors in pancreatic cancers (data not shown).

A Complex Stimulation Allows Compensation Between PI3K Isoforms in Pancreatic Cancer We next analyzed the activation of PI3K pathway upon serum stimulation in a time course manner. Serum led to an increased activation of pAkt compared to starved conditions (data not shown). Long-term inhibition of all PI3Ks or of p110γ led to a re-activation of p-Akt as early as 1 h after the initial inhibition, and prolonged pAkt activation up to 48 h (data not shown) Inhibition of p110α or combined inhibition of p110γ and p110α did not show such upregulation of pAkt levels upon PI3K inhibition (data not shown). Serum enables the compensation by p110α of PI3Ks inhibition; only a strong inhibition of p110α by a p110α-selective inhibitor prevents this re-activation of pAkt.

Figure 1B:
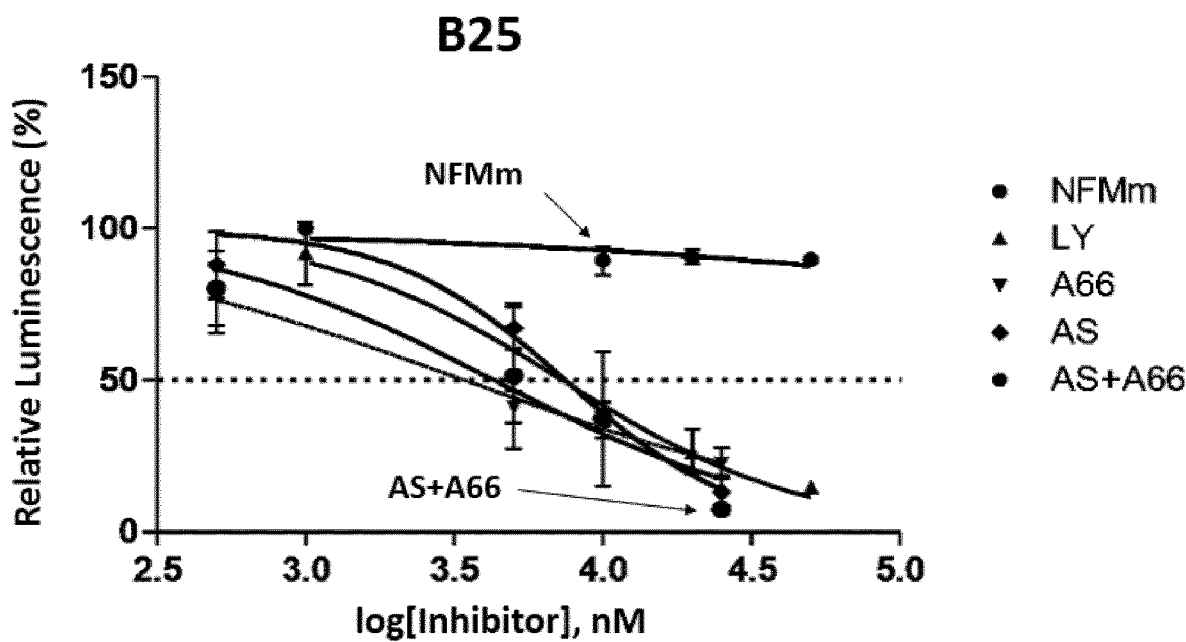
Figure 1C:
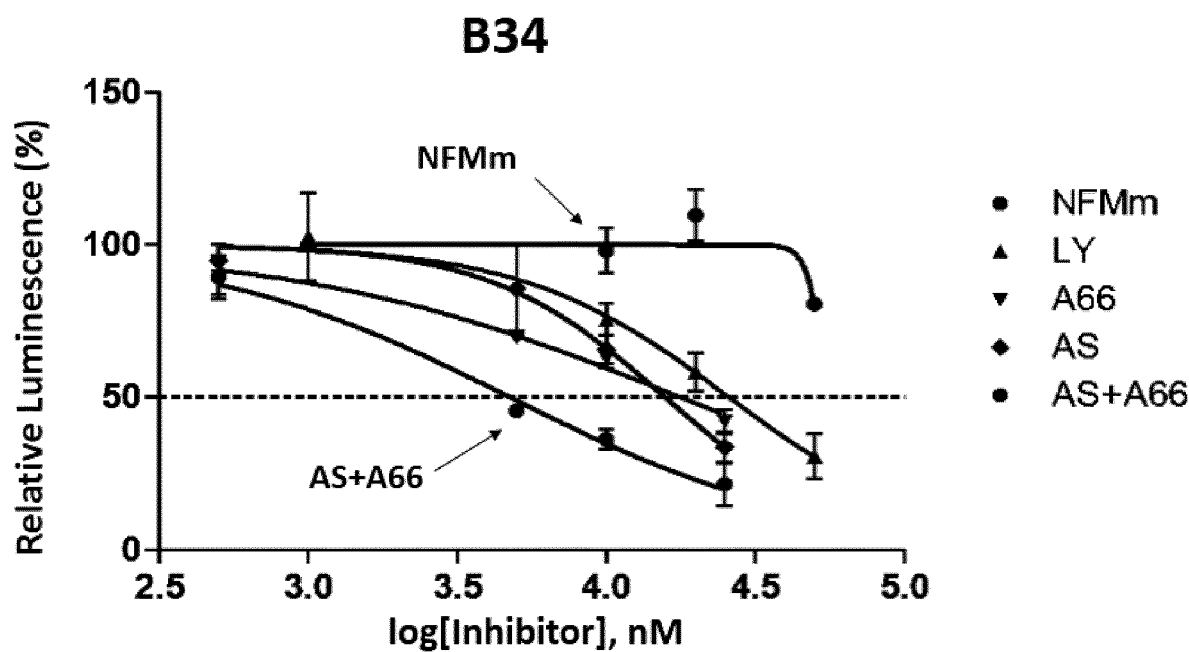
Figure 1D:
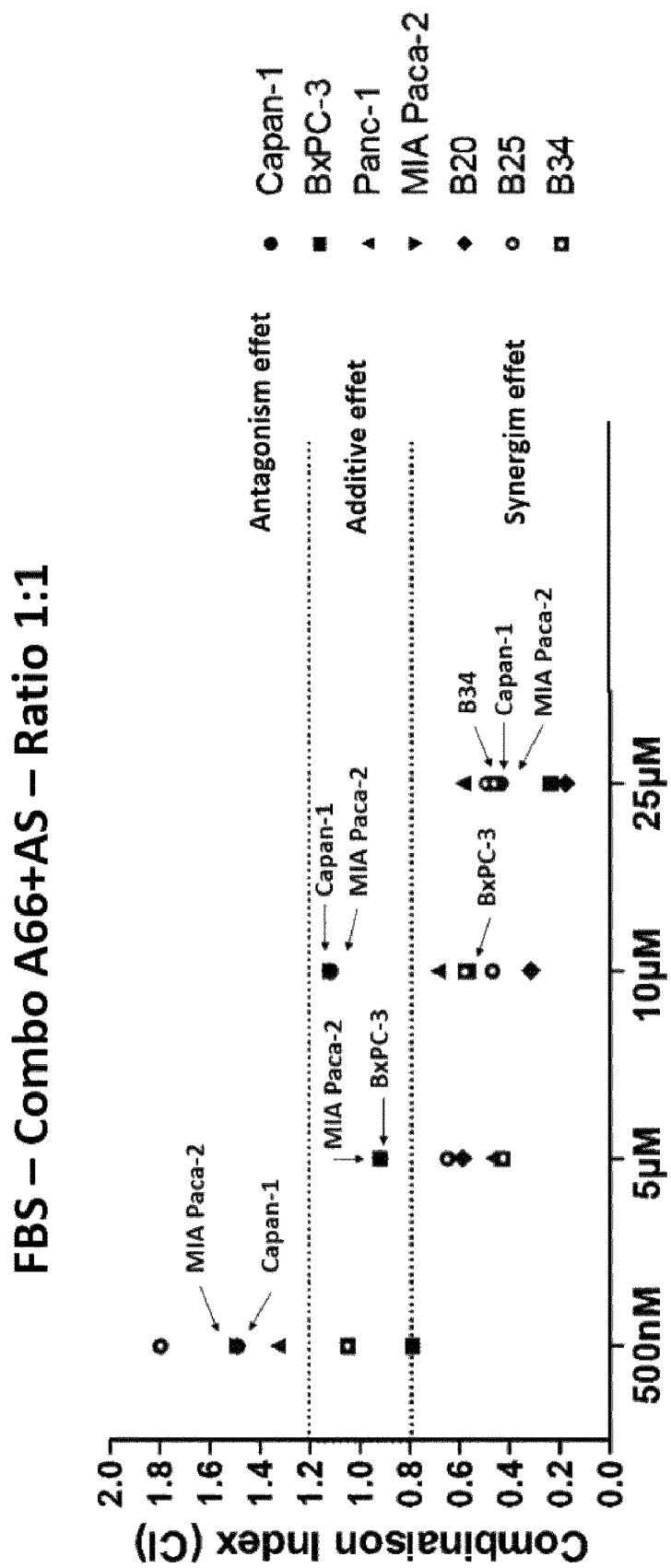
Figure 2A:
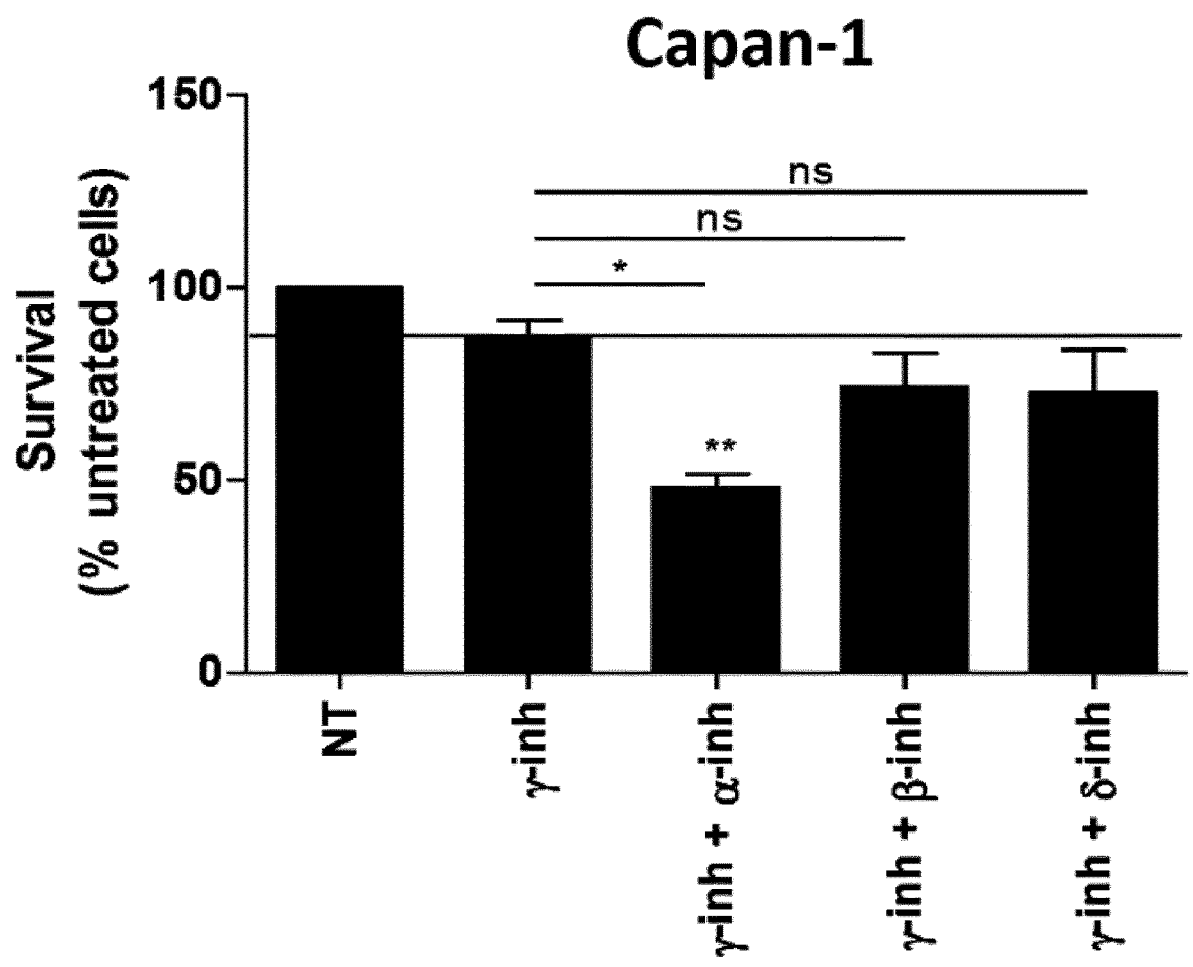
Figure 2B:
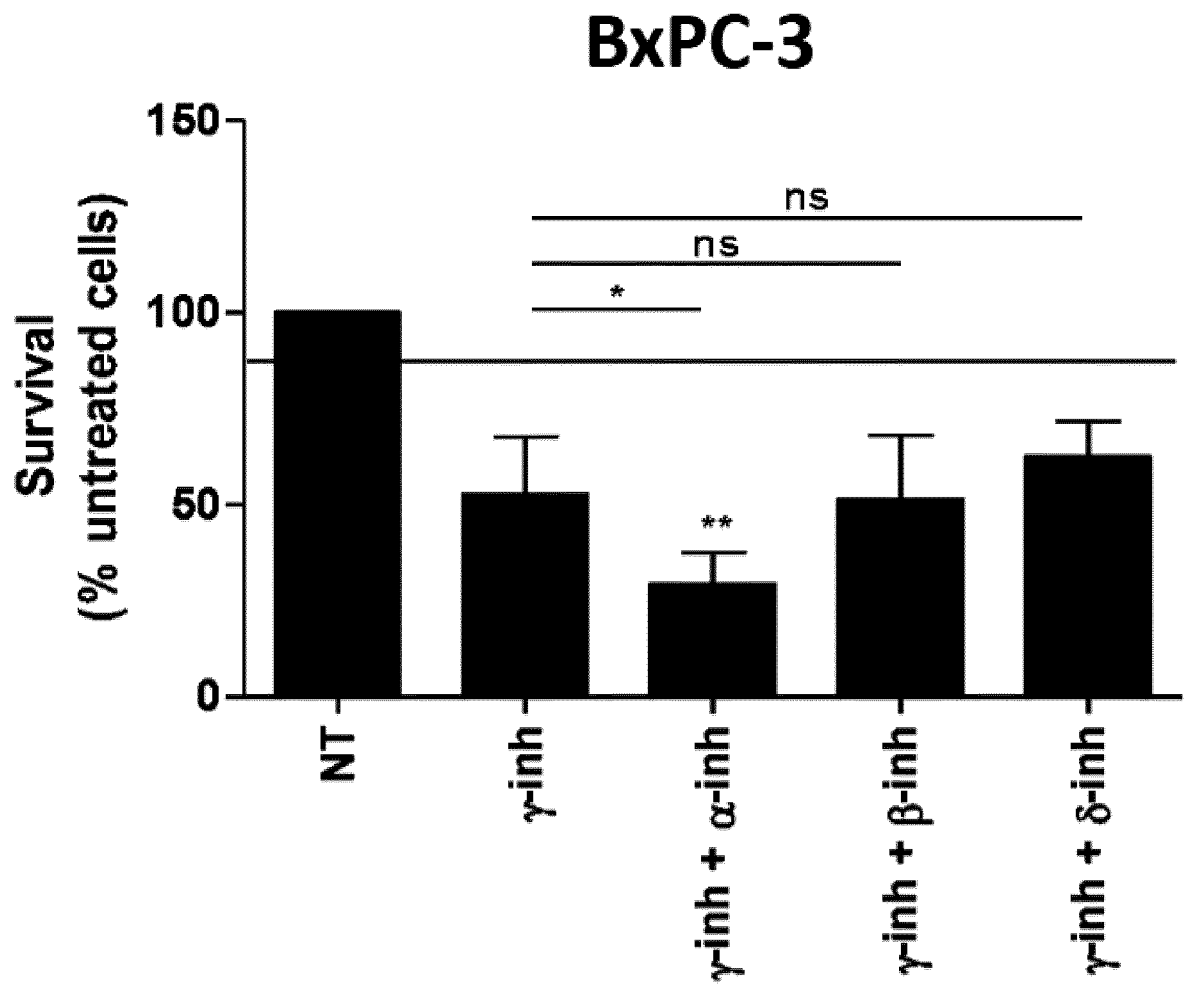
Figure 2C:
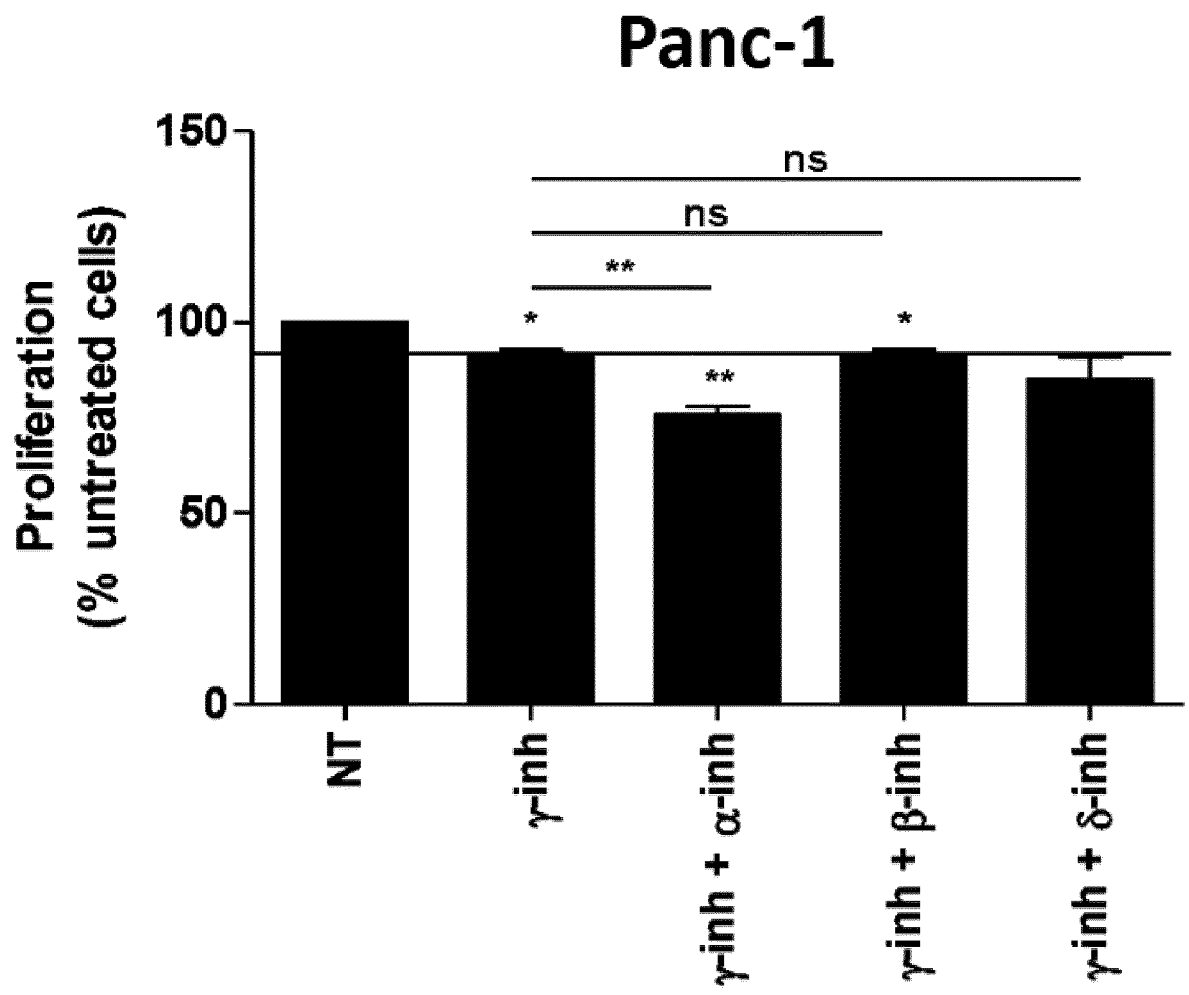
Figure 2D:
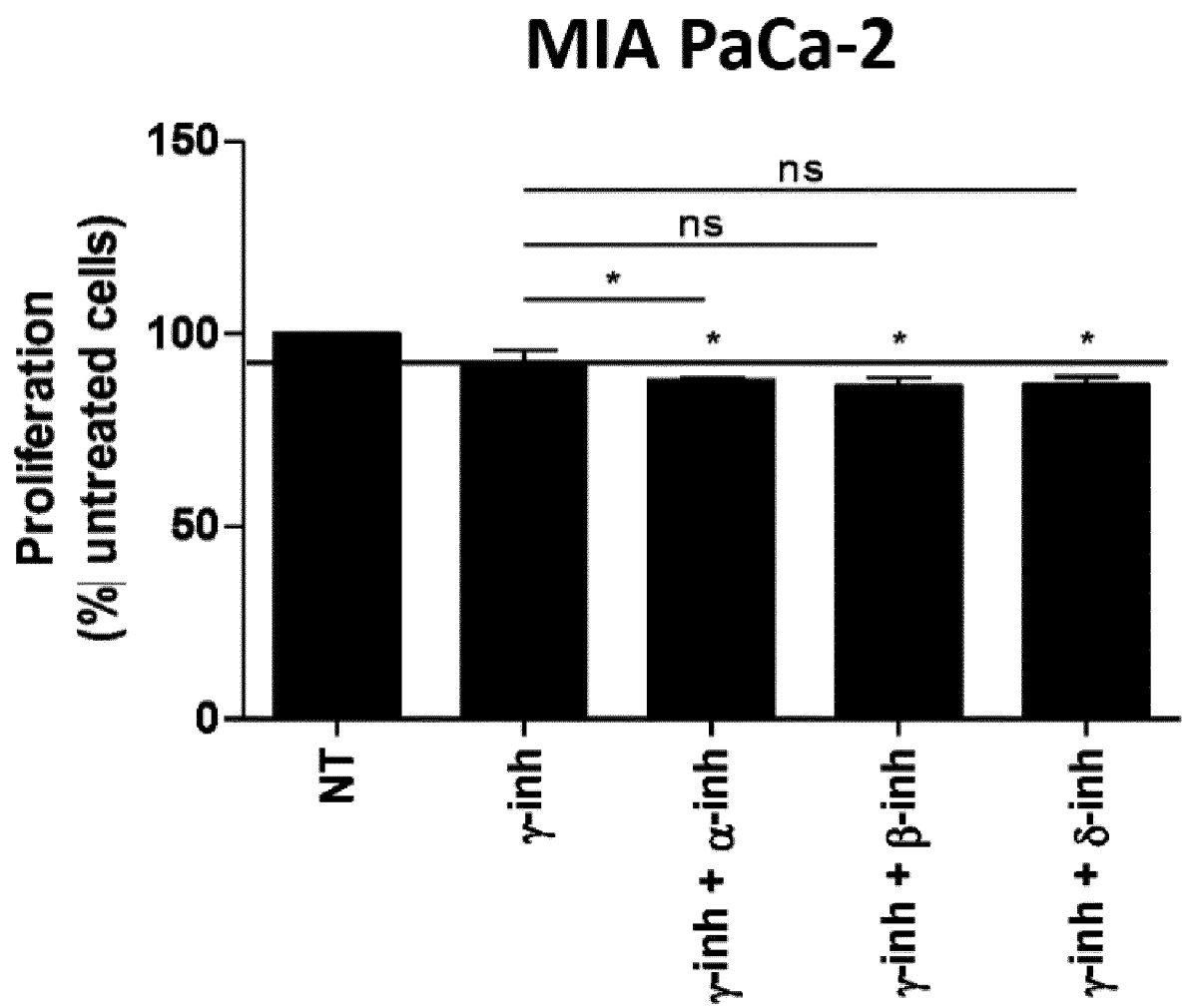

Inhibiting Selective Signalling of p110α Prevents Pancreatic Cancer Resistance to p110γ Inhibition Analysis of functions regulated selectively by p110α at 24 h showed that p110α regulated additional functions and cellular component compared to all PI3Ks or p110γ only. We thus tested the combination of p110α- and p110γ-selective inhibitors in three human pancreatic cancer primary cultures. We observed that the combination of p110α- and p110γ-inhibition led to an increase sensitivity to PI3K inhibition as assessed with the measurements of numbers of organoids, of their size and of their metabolism (FIGS. 1A-C). In all cell lines tested and in all human primary samples, combined inhibition of p110α and p110γ had a synergistic action (FIG. 1D). We observed that the upregulation of pAkt by p110γ inhibition is found in all cell lines tested (data not shown). Combination of p110γ inhibitor with other isoforms p110β or p110δ inhibitors did not lead to this synergistic action (FIG. 2). Combined p110α and p110γ inhibition is the most efficient strategy for pancreatic cancer patients.

Isoform-Selective Downstream Targets could Explain Long-Term Isoform-Selective Action in Pancreatic Cancer We next wondered if the phosphopeptides selectively regulated at long-term by either p110α or p110γ could correlate with the effect of each PI3K inhibitors. pHDGF, pTHOC2 and pGIGYF2 changes in ratios correlated with PI3K action on pancreatic cell numbers. Interestingly, change of phosphorylation levels of the known targets of PI3K as assessed by WB did not correlated with the cellular action in the four pancreatic cancer cell lines. Amongst the selective targets of each PI3K, some phosphopeptides could explain the selectivity of action of PI3K inhibitors.

Discussion:

Whether critical signal nodes can be circumvented is a fundamental question in tumoral biology. Using a phospho-proteomics screen, we demonstrate how each class I PI3K regulates cell/proliferation survival but have differential signalling state in the tumoral cells. In PDAC, this reciprocal crossregulation supplement cell-autonomous oncogenic signalling to control cell proliferation/survival. Reciprocal class I PI3K signalling is the exclusive product of pressure of inhibition of pathways and is independent of the level of expression of each PI3K. However, a selective and strong inhibition of the most important PI3K isoforms is able to inhibit selective pathways which allow the efficiency of PI3K targeting drugs.

Preclinical data in pancreatic cancer have been suggesting since a long time that PI3K could be a target for PDAC patients (initial study using wortmannin in xenografts of Human pancreatic cancer cell lines [22]. Many studies tried to directly target the downstream effector mTOR-containing protein complex, mTORC1, using rapamycin and related rapalogs. However, negative feedback loops that activate Akt in response to a prolonged mTORC 1 inhibition promoted growth and survival of various solid tumours [17, 23-25]. For PDAC, initial studies have focused on inhibition of mTOR with the rapalogs but also with ATP-competitive-inhibitors which block mTORC1 and mTORC2 activation. Three phase II trials have failed to demonstrate the therapeutic activity of rapalogs (Sirolimus®, Everolimus®, Temsirolimus®) in Gemcitabine-resistant metastatic pancreatic cancer, while the drugs were well tolerated [17, 26, 27].

NVP-BEZ235, a dual PI3K/mTOR inhibitor, was tested in pancreatic cancer models because of its ability not to induce mTOR-dependent specific feedback on Akt. Venkannagari et al. demonstrated that this inhibitor reduced Panc1 cells and human primary Akt2-amplified pancreatic tumour cell growth [28]. Moreover, they demonstrated an additive effect with panobinostat, a pan-histone deacetylase inhibitor. Eser et al. showed in the in situ pancreatic cancer model, KPC encompassing a mutation of Kras and p53 in the pancreas, that targeting PI3K signalling pathway with GDC-0941, a pan-PI3K inhibitor, actually tested in clinical trials [29, 30], is able to efficiently prevent KPC pancreatic tumour growth for 14 days. As opposed to control animals which showed rapid disease progression, GDC-0941 treated animals displayed stable disease 14 days after established tumours detection. Moreover, primary patient-derived PDAC cells orthotopically transplanted into immunodeficient mice responded the same way to GDC-0941, demonstrating that PI3K signalling is necessary for tumour cell proliferation and tumour maintenance [31].

Many groups also tested the targeting of PI3K signal node in combination with standard treatments or new targeted therapies in relevant pancreatic cancer mouse models. The combination of GDC-0941 and AZD6244, a MEK inhibitor, in vivo, given after the establishment of BxPC-3 cancer cells xenografts was compared to the respective treatments alone. Surprisingly, in contrary to AZD6244-based treatment, GDC-0941 did not impair tumour volumes. The combination treatment did not statistically improve AZD6244 effect. This might be explained by the genetic background of BxPC-3 cancer cells which do not carry oncogenic Kras mutation and thus are not "addicted" to PI3K signalling pathway [32]. However, murine pancreatic cancer cell lines harbouring an inducible mutated-Kras expression upon doxycyclin treatment, when implanted into nude mice with doxycyclin, developed AZD6244-resistant tumours. This resistance was due to an aberrant RTK-mediated PI3K/Akt signalling pathway activation upon MEK inhibition. Additive BEZ-235 treatment or a cocktail of RTK inhibitors were able to prevent this process [33]. Similarly, inhibition of MEK has a minimal anti-tumoral activity because it elicits a strong feedback activation of Akt [16]. Using the most relevant KPC mouse model that rapidly develops PDAC, Alagesan et al. tested AZD6244 (MEK inhibitor), BKM120 or GDC-0941 (class I PI3K inhibitors). They performed 2 sets of in vivo experiments. First they started treatments at 8 weeks of age, a time point when only preinvasive pancreatic ductal lesions are present. While AZD6244 and BKM120 alone had nearly no effect on murine lethality induced by mutated Kras and p53, the combination of both agents gave the strongest protective effect, nearly doubling survival rate. Despite the extension lifespan of KPC mice upon AZD/BKM treatment, all mice eventually developed pancreatic tumours. In the second therapeutic setup, 12-week old KPC mice were randomized into different groups. While control-, AZD- and BKM-treated mice developed progressive disease, 7 day-treated AZD/BKM KPC mice displayed an initial reduction of tumour size. After 2 or 3 weeks of treatment, those mice showed increased size of tumours demonstrating that the initial effect is transient and strongly indicating that compensatory mechanisms on other signalling pathways are involved [34]. Similar results were obtained on tumour induced by other genetic alteration such as KrasG12D; Cre; p16+/−; mice [35]. The current data for pancreatic cancer treatment with PI3K-targeting drugs suggest that pan-PI3K inhibition alone is not sufficient to abrogate pancreatic tumour growth, but its inhibition can abrogate resistance of tumours upon MEK inhibition. PI3K signal alone should be targeted in combination with other conventional or targeted therapies.

Indeed, despite the wide array of evidence involving PI3K/Akt signalling in this cancer, the strategies to hit PI3K/Akt/mTOR pathway have in some context failed to demonstrate attractive therapeutic activity. For example, in pancreatic cancer cells, dual PI3K-mTOR inhibition induces rapid over-activation of MAPK pathway through a PI3K-independent pathway [36]. There is an urgent need to improve those therapeutical strategies and prevent feedback loops involved in pancreatic cancer progression upon pan-PI3K treatment. This will be critical in the future establishment of new standard of care treatments. One strategy consists into identifying the tumours which are more likely to respond to each drug. It was indeed recently shown that p27kip1 haploinsufficiency of the the cyclin-dependent kinase inhibitor accelerated Kras-driven cancer development in vivo [37]. Furthermore, p27kip1 controlled NVP-BEZ235 (PI3K/mTOR inhibitor) sensitivity in a gene dose dependent fashion in murine PDAC cells and lowering of p27kip1 decreases NVP-BEZ235 response in murine PDAC cell lines. Similarly, preclinical anti-tumoral activity of the mTORC inhibitor is dependent on the genetic alteration inducing the pancreatic cancer, with PDAC arising from pten (deficient background being more sensitive to the drug [38].

Another strategy to be tested in the future could be to use isoform-selective drugs at high dose which we show as likely to induce less feedback and resistance mechanism. Combination of a global PI3K inhibitor GDC-0941 with Gemcitabine alone, the current standard of care, is not synergistic on in situ and xenografts pancreatic tumour regression [35].

So far, only multi-combinatorial therapies gave a positive clinical outcome for this pathology. Isoform-specific drugs are expected to induce less secondary effects and could thus be included in these multi-drug combinatorial therapies.

REFERENCES

Throughout this application, various references describe the state of the art to which this invention pertains. The disclosures of these references are hereby incorporated by reference into the present disclosure.

1. Vanhaesebroeck, B., et al., *The emerging mechanisms of isoform-specific PI3K signalling*. Nature Reviews Molecular Cell Biology, 2010. 11(5): p. 329-341.
2. Vanhaesebroeck, B., et al., *The emerging mechanisms of isoform-specific PI3K signalling*. Nat Rev Mol Cell Biol, 2010. 11(5): p. 329-41.
3. Al-Qassab, H., et al., *Dominant Role of the p110 beta Isoform of PI3K over p110 alpha in Energy Homeostasis Regulation by POMC and AgRP Neurons*. Cell Metabolism, 2009. 10(5): p. 343-354.
4. Gratacap, M.-P., et al., *Regulation and roles of PI3K beta, a major actor in platelet signaling and functions, in Advances in Enzyme Regulation*, Vol 51, L.W.G.W.C.E.F. Cocco, Editor. 2011. p. 106-116.
5. Graupera, M., et al., *Angiogenesis selectively requires the p110 alpha isoform of PI3K to control endothelial cell migration*. Nature, 2008. 453(7195): p. 662-U9.
6. Guillermet-Guibert, J., et al., *The p110 beta isoform of phosphoinositide 3 kinase signals downstream of G protein-coupled receptors and is functionally redundant with p110 gamma*. Proceedings of the National Academy of Sciences of the United States of America, 2008. 105(24): p. 8292-8297.
7. Martin, V., et al., *Deletion of the p110 beta isoform of phosphoinositide 3-kinase in platelets reveals its central role in Akt activation and thrombus formation in vitro and in vivo*. Blood, 2010. 115(10): p. 2008-2013.
8. Pons-Tostivint, E., B. Thibault, and J. Guillermet-Guibert, *Targeting PI3K Signaling in Combination Cancer Therapy*. Trends Cancer, 2017. 3(6): p. 454-469.
9. Vasudevan, K. M., et al., *AKT-independent signaling downstream of oncogenic PIK3CA mutations in human cancer*. Cancer Cell, 2009. 16(1): p. 21-32.
10. Castellano, E. and J. Downward, *RAS Interaction with PI3K: More Than Just Another Effector Pathway*. Genes Cancer, 2011. 2(3): p. 261-74.
11 Foukas, L. C., et al., *Critical role for the p110alpha phosphoinositide-3-OH kinase in growth and metabolic regulation*. Nature, 2006. 441(7091): p. 366-70.
12. Costa, C., et al., *Measurement of PIP3 levels reveals an unexpected role for p110beta in early adaptive responses to p110alpha-specific inhibitors in luminal breast cancer*. Cancer Cell, 2015. 27(1): p. 97-108.
13. Schwartz, S., et al., *Feedback suppression of PI3Kalpha signaling in PTEN-mutated tumors is relieved by selective inhibition of PI3Kbeta*. Cancer Cell, 2015. 27(1): p. 109-22.
14. Leroy, C., et al., *Activation of IGF1R/p110beta/AKT/mTOR confers resistance to alpha-specific PI3K inhibition*. Breast Cancer Res, 2016. 18(1): p. 41.
15. Schlieman, M. G., et al., *Incidence, mechanism and prognostic value of activated AKT in pancreas cancer*. Br J Cancer, 2003. 89(11): p. 2110-5.
16. Kong, B., et al., *A subset of metastatic pancreatic ductal adenocarcinomas depends quantitatively on oncogenic Kras/Mek/Erk-induced hyperactive mTOR signalling*. Gut, 2015. 65(4): p. 647-57.
17. Wolpin, B. M., et al., *Oral mTOR inhibitor everolimus in patients with gemcitabine-refractory metastatic pancreatic cancer*. J Clin Oncol, 2009. 27(2): p. 193-8.
18. Baer, R., et al., *Pancreatic cell plasticity and cancer initiation induced by oncogenic Kras is completely dependent on wild-type PI3-kinase p110alpha*. Genes Dev, 2014. 28(23): p. 2621-35.
19. Edling, C. E., et al., *Key role of phosphoinositide 3-kinase class IB in pancreatic cancer*. Clin Cancer Res, 2010. 16(20): p. 4928-37.
20. Cancer Genome Atlas Research Network. Electronic address, a.a.d.h.e. and N. Cancer Genome Atlas Research, *Integrated Genomic Characterization of Pancreatic Ductal Adenocarcinoma*. Cancer Cell, 2017. 32(2): p. 185-203 e13.
21. Geiger, T., et al., *Use of stable isotope labeling by amino acids in cell culture as a spike-in standard in quantitative proteomics*. Nat Protoc, 2011. 6(2): p. 147-57.
22. Ng, S. S., et al., *Wortmannin inhibits pkb/akt phosphorylation and promotes gemcitabine antitumor activity in orthotopic human pancreatic cancer xenografts in immunodeficient mice*. Clin Cancer Res, 2001. 7(10): p. 3269-75.
23. O'Reilly, K. E., et al., *mTOR inhibition induces upstream receptor tyrosine kinase signaling and activates Akt*. Cancer Res, 2006. 66(3): p. 1500-8.
24. Carracedo, A., et al., *Inhibition of mTORC1 leads to MAPK pathway activation through a PI3K-dependent feedback loop in human cancer*. J Clin Invest, 2008. 118(9): p. 3065-74.
25. Vilar, E., J. Perez-Garcia, and J. Tabernero, *Pushing the envelope in the mTOR pathway: the second generation of inhibitors*. Mol Cancer Ther, 2011. 10(3): p. 395-403.
26. Garrido-Laguna, I., et al., *Integrated preclinical and clinical development of mTOR inhibitors in pancreatic cancer*. Br J Cancer, 2010. 103(5): p. 649-55.
27. Javle, M. M., et al., *Inhibition of the mammalian target of rapamycin (mTOR) in advanced pancreatic cancer: results of two phase II studies*. BMC Cancer, 2010. 10: p. 368.
28. Venkannagari, S., et al., *Superior efficacy of co-treatment with dual PI3K/mTOR inhibitor NVP-BEZ235 and pan-histone deacetylase inhibitor against human pancreatic cancer*. Oncotarget, 2012. 3(11): p. 1416-27.
29. Fruman, D. A. and C. Rommel, *PI3K and cancer: lessons, challenges and opportunities*. Nat Rev Drug Discov, 2014. 13(2): p. 140-56.
30. Thorpe, L. M., H. Yuzugullu, and J. J. Zhao, *PI3K in cancer: divergent roles of isoforms, modes of activation and therapeutic targeting*. Nat Rev Cancer, 2015. 15(1): p. 7-24.
31. Eser, S., et al., *Selective requirement of PI3K/PDK1 signaling for Kras oncogene-driven pancreatic cell plasticity and cancer*. Cancer Cell, 2013. 23(3): p. 406-20.
32. Zhong, H., et al., *Synergistic effects of concurrent blockade of PI3K and MEK pathways in pancreatic cancer preclinical models*. PLoS One, 2013. 8(10): p. e77243.
33. Pettazzoni, P., et al., *Genetic Events That Limit the Efficacy of MEK and RTK Inhibitor Therapies in a Mouse Model of KRAS-Driven Pancreatic Cancer*. Cancer Res, 2015. 75(6): p. 1091-101.

34. Alagesan, B., et al., *Combined MEK and PI3K inhibition in a mouse model of pancreatic cancer.* Clin Cancer Res, 2015. 21(2): p. 396-404.
35. Junttila, M. R., et al., *Modeling targeted inhibition of MEK and PI3 kinase in human pancreatic cancer.* Mol Cancer Ther, 2015. 14(1): p. 40-7.
36. Soares, H. P., et al., *Dual PI3K/mTOR Inhibitors Induce Rapid Overactivation of the MEK/ERK Pathway in Human Pancreatic Cancer Cells through Suppression of mTORC2.* Mol Cancer Ther, 2015. 14(4): p. 1014-23.
37. Diersch, S., et al., *Efemp1 and p27(Kip1) modulate responsiveness of pancreatic cancer cells towards a dual PI3K/mTOR inhibitor in preclinical models.* Oncotarget, 2013. 4(2): p. 277-88.
38. Morran, D. C., et al., *Targeting mTOR dependency in pancreatic cancer.* Gut, 2014. 63(9): p. 1481-9.
39. Baer, R., et al., *Implication of PI3K/Akt pathway in pancreatic cancer: When PI3K isoforms matter?* Adv Biol Regul, 2015. 59: p. 19-35.
40. Lee, K. M., et al., *Immortalization with telomerase of the Nestin-positive cells of the human pancreas.* Biochem Biophys Res Commun, 2003. 301(4): p. 1038-44.
41. Campbell, P. M., et al., *Ras-driven transformation of human nestin-positive pancreatic epithelial cells.* Methods Enzymol, 2008. 439: p. 451-65.
42. Furukawa, T., et al., *Long-term culture and immortalization of epithelial cells from normal adult human pancreatic ducts transfected by the E6E7 gene of human papilloma virus 16.* Am J Pathol, 1996. 148(6): p. 1763-70.
43. Livak, K. J. and T. D. Schmittgen, *Analysis of relative gene expression data using real-time quantitative PCR and the 2(−Delta Delta C(T)) Method.* Methods, 2001. 25(4): p. 402-8.
44. Wisniewski, J. R., et al., *Universal sample preparation method for proteome analysis.* Nat Methods, 2009. 6(5): p. 359-62.
45. Larsen, M. R., et al., *Highly selective enrichment of phosphorylated peptides from peptide mixtures using titanium dioxide microcolumns.* Mol Cell Proteomics, 2005. 4(7): p. 873-86.
46. Jensen, S. S. and M. R. Larsen, *Evaluation of the impact of some experimental procedures on different phosphopeptide enrichment techniques.* Rapid Commun Mass Spectrom, 2007. 21(22): p. 3635-45.
47. Aryal, U. K. and A. R. Ross, *Enrichment and analysis of phosphopeptides under different experimental conditions using titanium dioxide affinity chromatography and mass spectrometry.* Rapid Commun Mass Spectrom, 2010. 24(2): p. 219-31.
48. Ycart, B., F. Pont, and J. J. Fournie, *Curbing false discovery rates in interpretation of genome-wide expression profiles.* J Biomed Inform, 2014. 47: p. 58-61.
49. Chou, T. C., *Drug combination studies and their synergy quantification using the Chou-Talalay method.* Cancer Res, 2010. 70(2): p. 440-6.
50. Chou, T. C. and P. Talalay, *Quantitative analysis of dose-effect relationships: the combined effects of multiple drugs or enzyme inhibitors.* Adv Enzyme Regul, 1984. 22: p. 27-55.

The invention claimed is:

1. A method of treating pancreatic cancer in a patient in need thereof comprising administering to the patient a therapeutically effective combination of at least one small molecule p110α selective inhibitor and at least one small molecule p110γ selective inhibitor.

2. The method of claim 1 wherein the pancreatic cancer is pancreatic ductal adenocarcinoma.

* * * * *